United States Patent [19]
Ertel

[11] 4,297,519
[45] Oct. 27, 1981

[54] PROCESS FOR THE PREPARATION OF 2-NITROBENZALDEHYDE

[75] Inventor: Werner Ertel, Wuppertal, Fed. Rep. of Germany

[73] Assignee: Bayer Aktiengesellschaft, Leverkusen, Fed. Rep. of Germany

[21] Appl. No.: 125,617

[22] Filed: Feb. 28, 1980

Related U.S. Application Data

[63] Continuation-in-part of Ser. No. 8,633, Feb. 1, 1979, abandoned.

[30] Foreign Application Priority Data

Mar. 2, 1978 [DE] Fed. Rep. of Germany ....... 2808930

[51] Int. Cl.$^3$ ............................................. C07C 45/28
[52] U.S. Cl. .................................. 568/424; 568/936; 204/163 R
[58] Field of Search ........................................ 568/424

[56] References Cited

U.S. PATENT DOCUMENTS 2,888,488  5/1959  Nace ................................... 260/599

OTHER PUBLICATIONS

Epstein et al., Chemical Reviews, vol. 67, No. 3 (1967) pp. 247–260.

Primary Examiner—Bernard Helfin
Attorney, Agent, or Firm—Sprung, Felfe, Horn, Lynch & Kramer

[57] ABSTRACT

A process provided for the production of 2-nitrobenzaldehyde from 2-nitrotoluene, in which 2-nitrotoluene is converted, by bromination by a radical mechanism, to 2-nitrobenzyl bromide in the form of a bromination oil containing 20 to 50% or more of 2-nitrobenzyl bromide, and the bromination oil is oxidized directly with a mixture of dimethylsulphoxide and sodium bicarbonate in a weight ratio of 3:1 to 10:1 at temperatures of up to 100° C. and the 2-nitrobenzaldehyde is subsequently isolated via the bisulphite adduct, to give 2-nitrobenzaldehyde in high purity and high yield. The process also has the advantage of a very short reaction time. The 2-nitrobenzaldehyde produced is an important intermediate, for example in the production of pharmaceutically active 1,4-dihydropyridines.

2 Claims, No Drawings

PROCESS FOR THE PREPARATION OF 2-NITROBENZALDEHYDE

This application is a continuation-in-part of my application Ser. No. 8,633 filed Feb. 1, 1979 and now abandoned.

The present invention relates to a new chemically unobvious process for the production of 2-nitrobenzaldehyde, which compound can be used as in intermediate product for many purposes and in particular can be employed in the preparation of pharmaceutically active 4-(2-nitrophenyl)-1,4-dihydropyridine derivatives (compare German Patent Specification No. 1,670,827).

2-Nitrobenzaldehyde has hitherto only been accessible with difficulty, since most of the conventional processes of aldehyde synthesis fail when applied to this compound. German Auslegeschrift (German Published Specification) No. 2,415,062 comments in detail on the disadvantages of the processes known from the literature. The process of preparation described in the said Auslegeschrift (German Published Specification), from 2-nitrotoluene via the intermediate stages of 2-nitrophenylpyruvic acid and 2-nitrobenzal dichloride, admittedly gives 2-nitrobenzaldehyde in good yields, but as an industrial process is still expensive, as a result of the nature and number of the reaction steps and purification steps.

As a further method of preparation, DT-OS (German Published Specification) No. 2,708,115 describes the hydrolysis of 2-nitrobenzyl bromide to the corresponding alcohol, and subsequent oxidation with dilute nitric acid. Disadvantages of this process are the very long time requirement, since the hydrolysis alone requires 12 hours reaction time and the oxidation requires 5 hours reaction time, and the formation of nitric fumes which is unavoidable in an oxidation using nitric acid, and makes it necessary to take special precautionary measures.

Further, it is known to oxidize benzyl halides and benzyl tosylates with dimethylsulphoxide (DMSO) to give aldehydes (compare Kornblum et al., J. Am. Chem. Soc. 79 (1957), 6562). This publication also describes the reaction of p-nitrobenzyl bromide in DMSO to p-nitrobenzaldehyde, with a yield of 48%, as an example of the reaction. Higher yields of aldehydes can be obtained by starting from the corresponding tosylates (compare Kornblum et al., J. Am. Chem. Soc. 81 (1959), 4113–4).

According to the present invention there is provided process for the production of 2-nitrobenzaldehyde from 2-nitrotoluene, in which 2-nitrotoluene is converted, by bromination by a radical mechanism, to 2-nitrobenzyl bromide in the form of a bromination oil containing 20 to 50% or more of 2-nitrobenzyl bromide, and the bromination oil is oxidized directly with a mixture of dimethylsulphoxide and sodium bicarbonate in a weight ratio of 3:1 to 10:1 at temperatures of up to 100° C. and the 2-nitrobenzaldehyde is subsequently isolated via the bisulphite adduct. Preferably the bromination oil is oxidized with a mixture of dimethylsulphoxide and sodium bicarbonate in a weight ratio of 5:1.

This method surprisingly gives 2-nitrobenzaldehyde in high purity and high yield. On the basis of the results of Kornblum, mentioned above, it would have been expected that the reaction of 2-nitrobenzyl bromide would give lower yields than those obtained in the preparation from 4-nitrobenzyl bromide (48%), since steric hindrance of the reaction by the adjacent nitro group was to be expected and since, furthermore, a heavy loss was to be expected if 2-nitrobenzyl bromide was isolated from the crude bromination oil. Because of its low stability, 2-nitrobenzyl bromide cannot be distilled but can only be isolated by "freezing out".

2-Nitrobenzaldehyde is universally useful starting product for the preparation of numerous compounds and, as is shown by the above-mentioned patent applications and publications, there is an urgent need to prepare this compound in a simple and economical manner. The reaction, which has been known for more than 20 years, of p-nitrobenzyl bromide with DMSO to give p-nitrobenzaldehyde evidently led, to this day, to a prejudice against utilizing such reaction because of the low yield of the reaction product. Such prejudice has, however, been overcome by the procedure of the present invention.

It was not to be expected that on using the crude bromination oil instead of pure 2-nitrobenzyl bromide, such a smooth course of the reaction, with yields of more than 60% of 2-nitrobenzaldehyde, would be obtained. The very short reaction time is also surprising and advantageous. The mixture of bromination oil, DMSO and bicarbonate is generally heated to 100° C. in the course of 15–60 minutes, preferably about 30 minutes; thereafter the reaction ceases and working-up can be started immediately. Another advantage it the possibility of removing DMSO by distillation and re-using it repeatedly as an oxidising agent.

Further advantages which should be mentioned are:
(a) the danger of handling 2-nitrobenzyl bromide (severe exothermic decomposition at 110° C.) is eliminated by using the crude bromination oil, which still contains large proportions of 2-nitrotoluene,
(b) as a result of the rapid course of the reaction, the time required is low, and
(c) the removal of the remaining products of the reaction, namely water, $CO_2$, sodium bromide and dimethyl sulphide, presents no problems.

Using the process according to the invention it is thus possible to prepare 2-nitrobenzaldehyde in a technically simple, economical and time-saving manner.

The 2-nitrobenzaldehyde thus obtained can then be reacted further with β-dicarbonyl compounds and amines to give pharmacologically active 1,4-dihydropyridines (compare DT-OS (German Published Specification) No. 1,670,827=U.S. Pat. Nos. 3,799,934, 3,932,645 and 3,644,627).

The preparation of the bromination oil or of the 2-nitrobenzyl bromide is advantageously carried out by radical side chain bromination of 2-nitrotoluene. This reaction can be carried out under UV-light or infrared light or with N-bromosuccinimide or by means of peroxide catalysts (compare DT-OS (German Published Specification) No. 2,614,485. In every case, a mixture of 2-nitrobenzyl bromide and unconverted 2-nitrotoluene is obtained.

The following Examples illustrate the preparation of bromination oil according to example 3 of DT-OS No. 2.614.485.

EXAMPLE A

A solution of 27,5 g of 2-Nitrotoluene in 130 ml CCl₄ is treated under reflux with a solution of bromine in CCl₄(10 Vol. %) and simultaneously in the same amounts with 1,25 weight percent solution of diisopropyl-peroxide-dicarbonate in CCl$_4$ until the combination oil is containing 21,7% of 2-Nitrobenzyl bromide (the course of the reaction is controlled by gas chromatographic-analysis.

EXAMPLE B

The reaction is carried out according to Example A until the bromination oil is containing 32,0% of 2-Nitrobenzyl bromide.

The following Examples illustrate the preparation of 2-Nitrobenzaldehyde starting from the bromination oil, prepared as described above.

PREPARATION EXAMPLE 1

100 g of "bromination oil"+ are run into a mixture of 500 ml of DMSO and 100 g of sodium bicarbonate under nitrogen. The batch is heated to 100° C. in the course of 30 minutes, whilst stirring. It is then cooled to 50° C. and 350 to 400 ml of DMSO are distilled off at this temperature and 2 to 5 mm Hg. The residue is stirred with 500 ml of toluene. The sodium bromide and unconverted sodium bicarbonate are filtered off and the filter cake is rinsed with 200 ml of toluence. The solid is discarded. A solution of 80 g of sodium pyrosulphite in 120 ml of water is added to the filtrate, whilst stirring. After adding 120 g of ice, the mixture is stirred thoroughly for 1 hour. After adding a further 200 ml of water, the phases are separated. 200 ml of toluene are added to the aqueous phase and the latter is rendered alkaline to pH 12 with 45% strength sodium hydroxide solution. In doing so, the temperature rises to 35°–40° C. The phases are separated, the aqueous phase is discarded and the toluene phase is washed with 50 ml of water and then dried over magnesium sulphate. After filtering to remove the drying agent, the solution is evaporated in vacuo. The residue—a yellow oil—solidifies on cooling to give yellow solid 2-nitrobenzaldehyde.
+content of 2-Nitrobenzyl bromide: 49%

Yield: 24 g; Purity: 98%.

PREPARATION EXAMPLE 2

100 g of "bromination oil" (mixture of 2-nitrotoluene and 2-nitrobenzyl bromide; content of 2-nitrobenzyl bromide: 22.7%) are run into a mixture of 400 ml DMSO and 60 g of sodium bicarbonate under nitrogen. The mixture is heated to 100° in the course of 30 minutes, while stirring. It is then cooled to 50° C. and 200 ml of DMSO are distilled off at this temperature and 2 to 5 mm Hg. The residue is stirred with 400 ml toluene. The sodium bromide and unconverted sodium bicarbonate are filtered off and the filter cake is rinsed with 150 ml toluene. To the combined filtrates a solution of 17 g sodium bicarbonate in 100 ml of water is added, while stirring for thirty minutes. The phases are separated and the aqueous phase is rendered alkaline to pH 12 with 16 ml of sodium hydroxyd (aqueous solution of 35%). The 2-nitrobenzaldehyde precipitates as yellowish crystals. The solution is filtered off and the residue is washed with 100 ml of water and dried in vacuo.

Yield: 15 g (72% of theory); Purity: 98.0%

PREPARATION EXAMPLE 3

375 g of "bromination oil" (containing 21,7% of 2-nitrobenzyl bromide) are run into a mixture of 1500 ml of DMSO and 225 g of sodium bicarbonate under nitrogen during a period of 5 minutes at a temperature between 95° and 100° C. 980 ml of DMSO are distilled off under vacuo. The residue is stirred with 1000 ml of toluene, filtered off and the filter cake is rinsed with 300 ml of toluene. From the combined filtrate the toluene is distilled off and the residue is solved in 560 ml of heated toluene. At a temperature of 20° C. the solution of 64 g of sodium pyrosulfite in 375 ml of water is added and stirred for 30 minutes. The phases are separated and the aqueous phase is rendered alkaline to pH 12 with 35% strength sodium hydroxyde solution. The yellowish precipitate is filtered off, washed with ice-water and dried over silica gel.

Yielded: 40 g of yellow solid 2-nitrobenzaldehyde (66% of theory); Purity: 98%

PREPARATION EXAMPLE 4

According to the method of example 2 from 375 of "bromination oil" (content of 2-nitrobenzyl bromide 32%) 36,4 g of 2-nitrobenzaldehyde (60% of theory) are obtained.

Purity: 97%

What is claimed is:

1. A process for the preparation of 2-nitrobenzaldehyde from 2-nitrotoluene which comprises brominating 2-nitrotoluene by a radical mechanism, to 2-nitrobenzyl bromide in the form of a bromination oil containing 20 to 50% of 2-nitrobenzyl bromide, and then oxidizing said bromination oil directly with a mixture of dimethylsulphoxide and sodium bicarbonate in a weight ratio of 3:1 to 10:1 at temperatures of up to 100° C. and subsequently isolating the 2-nitrobenzaldehyde via the bisulphite adduct.

2. A process according to claim 1, in which the bromination oil is oxidized with a mixture of dimethylsulphoxide and sodium bicarbonate in a weight ratio of 5:1.

* * * * *